(12) United States Patent
Elliott

(10) Patent No.: US 7,497,821 B2
(45) Date of Patent: *Mar. 3, 2009

(54) METHOD OF PRESENTING AUDIBLE AND VISUAL CUES FOR SYNCHRONIZING THE BREATHING CYCLE WITH AN EXTERNAL TIMING REFERENCE FOR PURPOSES OF SYNCHRONIZING THE HEART RATE VARIABILITY CYCLE WITH THE BREATHING CYCLE

(75) Inventor: Stephen Bennett Elliott, Allen, TX (US)

(73) Assignee: Coherence LLC, Allen, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/692,370

(22) Filed: Mar. 28, 2007

(65) Prior Publication Data

US 2007/0173684 A1    Jul. 26, 2007

Related U.S. Application Data

(63) Continuation of application No. 10/802,456, filed on Mar. 18, 2004, now Pat. No. 7,255,672.

(51) Int. Cl.
*A61M 21/00* (2006.01)

(52) U.S. Cl. .................................................... 600/27

(58) Field of Classification Search ............. 600/26–28; 607/88; 368/10, 107–113; 434/238
See application file for complete search history.

(56) References Cited

U.S. PATENT DOCUMENTS

| 1,953,954 | A |  | 4/1934 | Constable |
| 4,711,585 | A |  | 12/1987 | Fresquez et al. |
| 5,734,795 | A |  | 3/1998 | Rogers |
| 6,212,135 | B1 | * | 4/2001 | Schreiber ................. 368/107 |
| 6,397,106 | B1 |  | 5/2002 | DeBrouse |
| 7,255,672 | B2 | * | 8/2007 | Elliott ...................... 600/27 |
| 2002/0051958 | A1 | * | 5/2002 | Khalsa ..................... 434/238 |
| 2002/0176591 | A1 |  | 11/2002 | Sandborn et al. |
| 2004/0148575 | A1 |  | 7/2004 | Haase |
| 2005/0149144 | A1 | * | 7/2005 | Siever .................... 607/45 |
| 2005/0209503 | A1 |  | 9/2005 | Elliott |

FOREIGN PATENT DOCUMENTS

| GB | 2381642 A | * | 5/2003 |
| GB | 2344288 |  | 4/2008 |

OTHER PUBLICATIONS

Bernardi, Luciano et al., "Effect of Rosary Prayer and Yoga Mantras on Autonomic Cardiovascular Rhythms: Comparative Study," bmj.com, Aug. 17, 2006, 5 pages.

Gardner-Gordan, Joy, "The Healing Voice, Traditional & Contemporary Toning, Chanting & Singing," 1993, 22 pages.

* cited by examiner

Primary Examiner—John P Lacyk
(74) Attorney, Agent, or Firm—Withrow & Terranova, PLLC

(57) ABSTRACT

The invention consists of a broad method of presenting audible and visual cues for synchronizing the breathing cycle with an external timing reference for purposes of synchronizing the heart rate variability cycle with the breathing cycle, thereby achieving coherence of the heart rate variability cycle. A family of audible and visual indicators is specified for purposes of communicating breathing phase, change of breathing phase, progression of time within a phase, and progression of the phase relative to the internal perception of the practitioner.

17 Claims, 8 Drawing Sheets

FIGURE 3

| Inhale | Color | Exhale |
|--------|--------|--------|
| 7 | purple | 7 |
| 6 | indigo | 8 |
| 5 | cyan | 9 |
| 4 | green | 10 |
| 3 | yellow | 11 |
| 2 | orange | 12 |
| 1 | red | 1 |

| 7 | purple |
| 6 | indigo |
| 5 | cyan |
| 4 | green |
| 3 | yellow |
| 2 | orange |
| 1 | red |

METHOD OF PRESENTING AUDIBLE AND VISUAL CUES FOR SYNCHRONIZING THE BREATHING CYCLE WITH AN EXTERNAL TIMING REFERENCE FOR PURPOSES OF SYNCHRONIZING THE HEART RATE VARIABILITY CYCLE WITH THE BREATHING CYCLE

CROSS-REFERENCE TO RELATED APPLICATIONS

The present application is a Continuation of U.S. patent application Ser. No. 10/802,456, Method of Presenting Audible and Visual Cues for Synchronizing the Breathing Cycle with an External Timing Reference for Purposes of Synchronizing the Heart Rate Variability Cycle with the Breathing Cycle, filed Mar. 18, 2004, currently pending, the disclosure of which is hereby incorporated by reference in its entirety.

This application is related to U.S. patent application Ser. No. 10/699,025, Method and System for Consciously Synchronizing the Breathing Cycle with the Natural Heart Rate Cycle, filed Nov. 3, 2003, U.S. patent application Ser. No. 10/784,266, Method and System for Synchronizing the Heart Rate Variability Cycle With the Breathing Cycle, filed Feb. 19, 2004, and U.S. patent application Ser. No. 11/060,671, Method of Presenting Audible and Visual Cues for Synchronizing the Breathing Cycle with an External Timing Reference for Purposes of Synchronizing the Heart Rate Variability Cycle with the Breathing Cycle, filed Feb. 18, 2005, which are hereby incorporated by reference in their entirety.

FIELD OF THE INVENTION

The present invention relates to human physiology, and in particular to a method and system for allowing a human subject to consciously control physiological processes, more particularly, it allows a human subject to achieve synchronization of the natural cycle of heart rate with the breathing cycle.

BACKGROUND OF THE INVENTION

The human heart is known to have its own nervous system and its own natural tendency toward rhythm. For purposes of this invention, there are two primary aspects to this rhythm, the heartbeat rate, and the rate at which the heartbeat rate changes otherwise known as heart rate variability. Heartbeat rate is usually specified in absolute number of heartbeats occurring during a specified period. Heartbeat rate variability, otherwise know as heart rate variability is the change in heartbeat rate as occurs during a specified period. Henceforth, heartbeat rate variability will be referred to as heart rate variability.

While the heart has its own tendency toward rhythm, it is closely coupled to breathing. The relationship is such that as inhalation occurs, the heartbeat rate tends to increase and as exhalation occurs, the heartbeat rate tends to decrease. It is important to note that while the heartbeat rate and breathing rate influence each other, the relationship is a plesiochronous one, that is, they are independent rhythms that strongly influence but do not directly control each other.

It is generally recognized that heart rate variability is an indicator of physiological and emotional state, that is, irregular incoherent heart rate variability indicates a condition of physiological/psychological stress. Alternatively, a highly regular coherent heart rate variability is indicative of a condition of physiological/psychological harmony.

Accordingly, it is highly desirable to achieve and maintain a highly coherent heart rate variability as life circumstances permit. This having been said, with proper training and the application of the present invention, it is possible for a human subject to rapidly achieve the desired state of high coherence of heart rate variability and to reinforce that coherence on an ongoing basis.

The present invention takes advantage of the relationship between the breathing cycle and the natural heart rate variability cycle to bring heart rate variability to the desired state of coherence and the human subject to the resultant state of physiological and emotional harmony. It accomplishes this via synchronization of the heart rate variability cycle with the breathing cycle. More specifically, it accomplishes this by providing audible and visual cues of varying formats which provide the practitioner with an accurate representation of a timing reference signal to which the breathing cycle is consciously synchronized.

SUMMARY OF THE INVENTION

As previously described, a relationship exists between the heartbeat rate specified in terms of heart rate variability, and the breathing cycle. While the heart has its own tendency toward a natural variable rhythm, there is a strong correlation with breathing according to this specific relationship: as inhalation occurs, there is a tendency for the heartbeat rate to increase, as exhalation occurs, there is a tendency for the heartbeat rate to decrease. In a relaxed or semi-active human subject, the effect of the breathing cycle on the heart rate variability cycle is extremely strong. In fact, the heart rate variability cycle will synchronize with the breathing cycle if the breathing cycle is highly attuned to the periodicity of the natural heart rate variability cycle. The nominal period of the typical human heart rate variability cycle is 11.76 seconds. Therefore, if the period of the breathing cycle is timed to 11.76 seconds, the heart rate variability cycle will synchronize with it, bringing the natural heart rate variability cycle into phase synchrony with the breathing cycle and thereby bringing the subject's heart rate variability cycle into the desired state of coherence.

The present invention accomplishes this by presenting the human subject with various forms of audible and visual cues individually or in combination to which the breathing cycle is consciously synchronized. These audible and visual cues are synchronous signals with a nominal periodicity of 11.76 seconds divided by 2, or 5.88 seconds, representing the 50% of the typical 11.76 second heart rate variability cycle and corresponding to 50% of the breathing cycle of like period, that is, the period of inhalation or exhalation. When the breathing is consciously synchronized to this external timing reference signal, the heart rate variability cycle will synchronize with it and remain synchronized as long as the breathing cycle remains aligned with the tuned external reference. In this way, the human subject can remain in the desired state of coherence of heart rate variability for extended periods of time. Ultimately, this builds familiarity with the desired psychophysiological condition such that synchronization with the external reference occurs subliminally and with continued practice, the state can be realized at will with or without the external timing reference signal.

For purposes of the present invention, we can consider the cycles of heart rate variability, the periodicity of increasing and decreasing of heartbeat rate, and the breathing cycle, the periodicity of inhalation and exhalation, to be two independent cycles. The relative synchronization of these cycles can vary between 0 and 180 degrees. When these cycles are completely out of phase, heart rate variability is maximally incoherent, when these cycles are completely in phase heart rate variability is maximally coherent.

BRIEF DESCRIPTION OF THE DRAWING FIGURES

The accompanying drawing figures incorporated in and forming a part of this specification illustrate several aspects of the invention, and together with the description serve to explain the principles of the invention.

Figure 4:
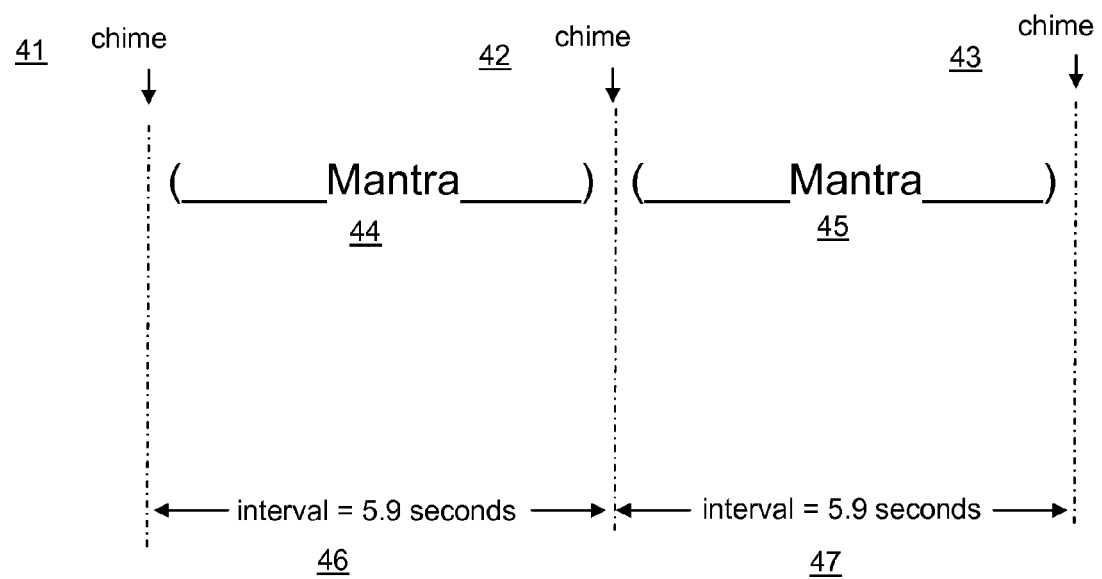
Figure 5:
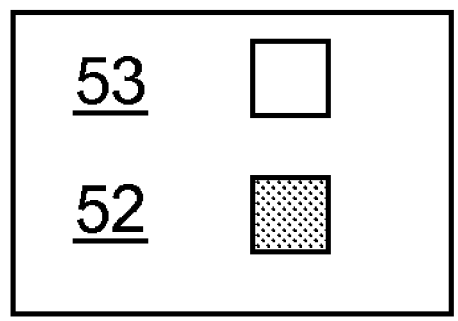
Figure 6:
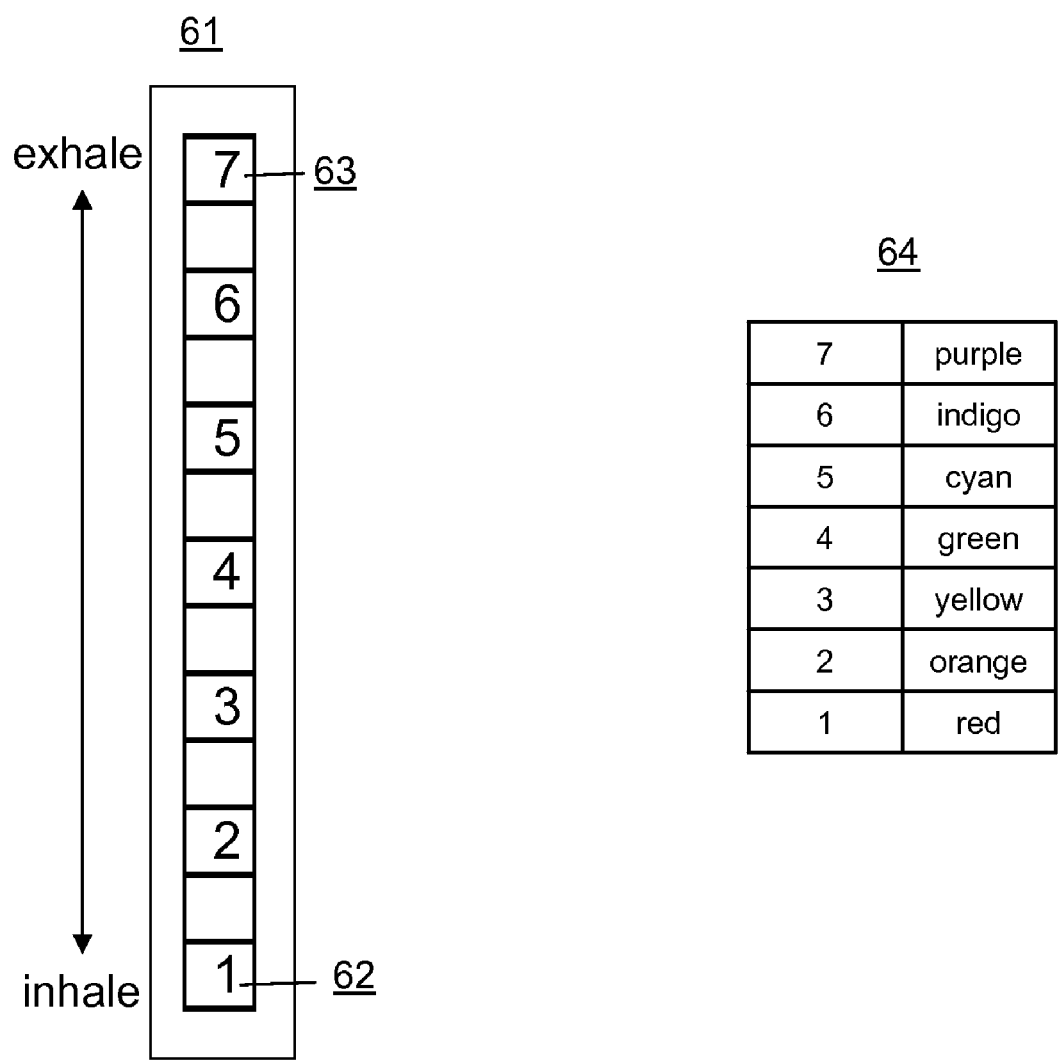
Figure 7:
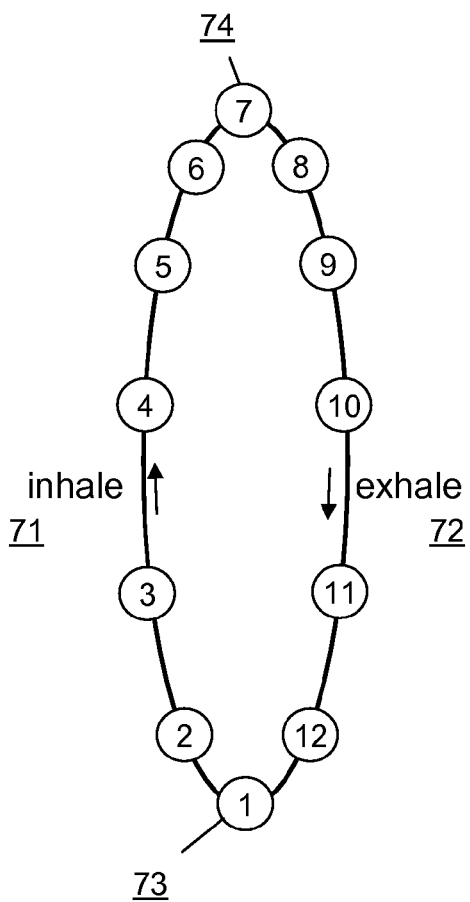

FIG. 3 presents an example of music with a tempo and audible cues specifically designed to align the breathing with a period of 5.9 seconds;

FIG. 4 presents an example of "mantra", a word or phrase that is repeated over and over, again designed to align the breathing with a period of 5.9 seconds;

FIG. 5 presents the most basic binary representation of the objective breathing cycle;

FIG. 6 presents a vertically-oriented thirteen (13) segment visual display;

FIG. 7 presents a vertically-oriented oval visual display with 12 segments; and

Figure 8:
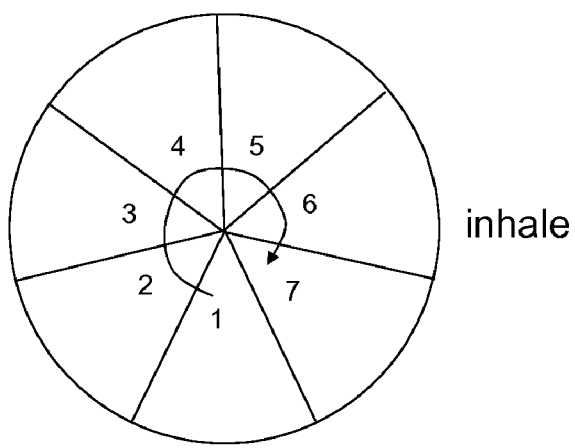
Figure 8:
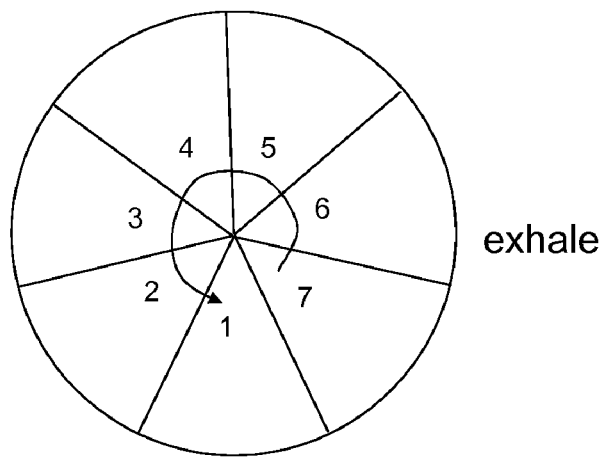

FIG. 8 presents a seven (7) sector circular visual display.

DETAILED DESCRIPTION OF THE PREFERRED EMBODIMENTS

The present invention describes a series of related audible and visual methods by which information relating to the periodicity of an external timing reference is conveyed to a human practitioner for purposes of synchronizing their breathing cycle with the external reference signal for purposes of synchronizing their heart rate variability cycle with their breathing cycle. It is understood that these methods may ultimately be instantiated in any number of devices employing numerous forms of media including audio tape, compact disk, digital video disk, computers, hardware or software synthesizers, telephones, cellular telephones, televisions or radio broadcast, clocks, watches, and purpose built specialty devices. Secondly, audible forms of the invention may be instantiated in any or all forms of audible media including but not limited to music, background ambience generators, clocks of varying variety such as grandfather clocks, alarm clocks, telephones, and audible network based services such as radio stations, internet based services, and purpose built specialty devices. Thirdly, it is understood that there are an infinite number of variations possible relative to how an external timing reference may be communicated to a human participant or participants for the purpose of consciously synchronizing the participant's breathing with the external timing reference. The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention allows a human subject to achieve coherence of heart rate variability by synchronizing the heart rate variability cycle with the breathing cycle. This is accomplished by providing an external timing reference in the form of an audible or visual signal, indicating when the subject should begin inhalation and when the subject should begin exhalation. In some cases, more complete information is provided indicating when the subject should begin inhalation, when the subject should end inhalation, when the subject should begin exhalation, and when the subject should end exhalation. This is repeated in a cyclic fashion, inhalation leading to exhalation, exhalation leading to inhalation, and so forth. The audible or visual reference signal is centered around the nominal frequency of 0.085 Hertz for a period of approximately 11.8 seconds, the center heart rate variability period of the typical human in a resting or semi-active state. When the typical human subject breathes at this rate, the heart rate variability cycle will synchronize with the breathing cycle, thereby maximizing the coherence of the heart rate variability cycle.

Figure 1:
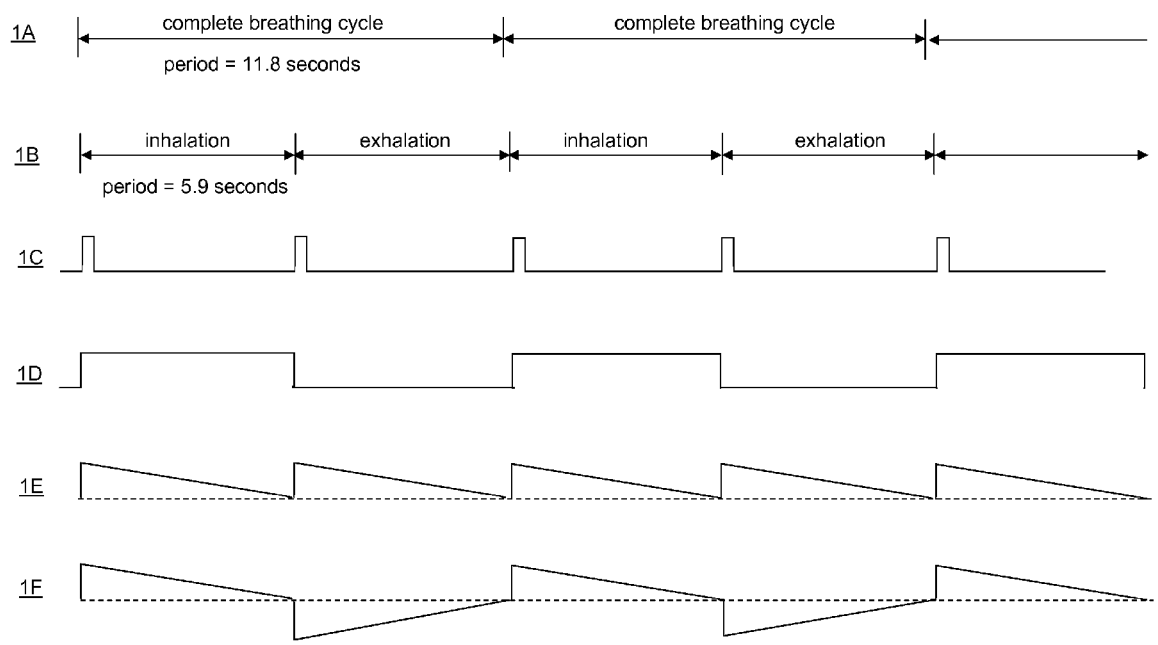
FIG. 1 depicts the fundamental periodicity and logical representations of audible and visual indicators of varying utility.

FIG. 1 presents basic timing and audible and visual functions in a logical format. The most basic information that must be conveyed to a subject or subjects practicing the method is the basic periodicity of the nominal 11.8 second breathing cycle 1A, divided by 2, yielding a 5.9 second period of inhalation and a 5.9 second period of exhalation 1B. This most basic indication is conveyed in the form of an audible or visual indicator of short duration 1C indicating when to change from inhalation to exhalation or when to change from exhalation to inhalation. 1D conveys this information as a change of phase, that is, a change from inhalation to exhalation or the reverse. Because very exacting coordination of the breath is required, a higher order signal indicating the moment of change as well as the progression of time is desirable 1E. Yet a further improvement that conveys change, progression, and distinguishes between inhalation and exhalation phases of activity is depicted by 1F.

To maximize heart rate variability coherence, it is extremely important that the timing of transitions from inhalation to exhalation and exhalation to inhalation be very exact. For this reason, it is highly desirable to provide the practitioner with audible or visual information such that they can understand breathing progression within a cycle, that is, within the 5.9 second period. By providing information relating to both progression and changes, the practitioner is much more able to align their breathing cycle with the external reference signal in an exacting fashion.

Figure 2:
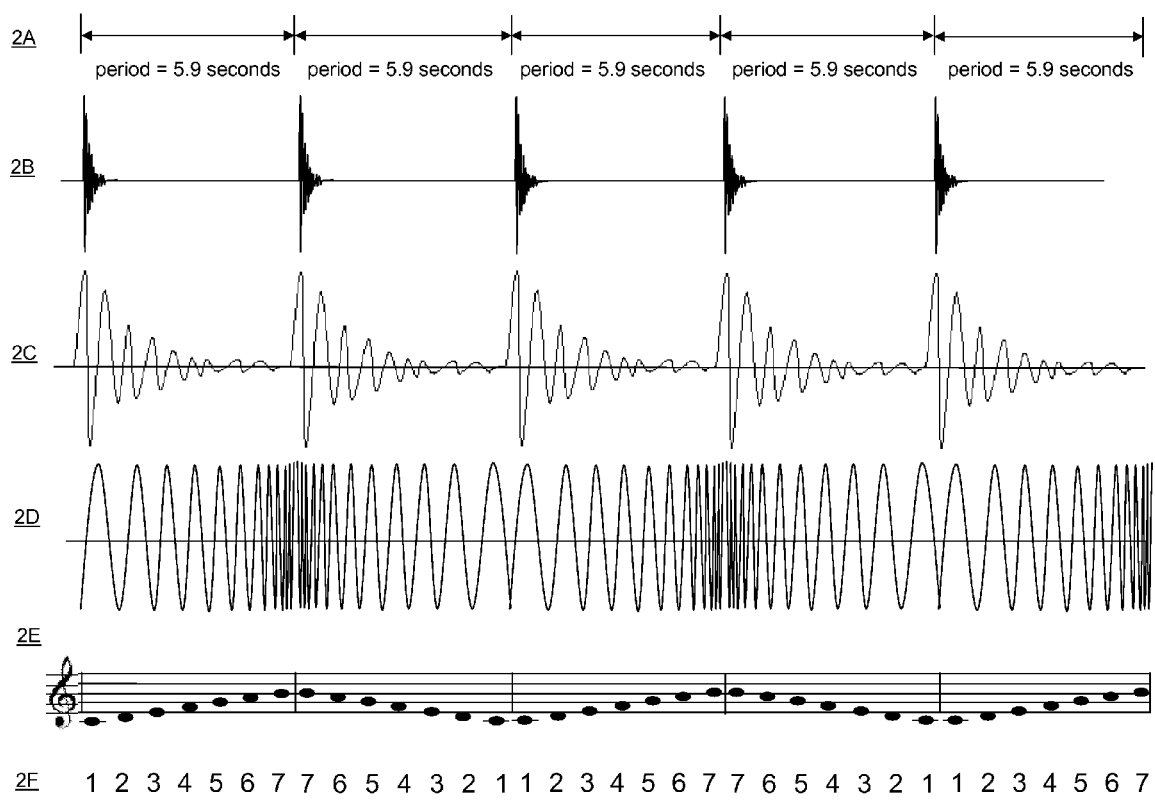
FIG. 2 depicts various methods of presenting audible information representing the synchronized breathing cycle.

With reference to FIG. 2, six basic methods for communicating audible information are exemplified. Each method will now be explained. 2A depicts the basic 5.9 second period to which the breath is aligned. 2B is the most basic case representing a tone, chime, or tick conveying information pertaining to the change of the breathing cycle, that is, with each tone, chime, or tick, the breathing cycle changes from inhalation to exhalation or from exhalation to inhalation.

2C depicts the case where information pertaining to both change and progression is provided. This case might be typified by plucking the string of a stringed instrument such as a guitar wherein there is a rapid attack followed by a gradual decay, the rapid attack representing the moment of change of the breathing cycle and the gradual decay representing the progression of the 5.9 second interval. In this exemplary embodiment, the rapid attack occurs every 5.9 seconds. The decay occurs across the 5.9 second interval such that the audio amplitude becomes zero just prior to the next attack, indicating to the practitioner that a change in breathing cycle is imminent.

2D employs frequency modulation as the basis of indicating changes and progression. In this case, an audible tone is varied in frequency, the highest and lowest frequencies indicating the moment of the change in the breathing cycle from inhalation to exhalation or from exhalation to inhalation, respectively. This method has the advantage of facilitating inhalation with increasing frequency and exhalation with decreasing frequency, a convention that is useful both for audible-only cuing and for combined audible and visual cuing as will be explained later.

2E employs a similar method to that of 2D but using discrete musical notes as opposed as a continuously variable tone. In this example, changes in breathing cycle occur in between the two highest and two lowest notes. In this example, 7 notes are employed to represent the 5.9 second period. It should be noted that 7 notes represents a preferred embodiment of the present invention and that the application of any number of notes within a 5.9 second period provided for purposes of synchronizing breathing either consciously or subconsciously is intended within the scope of this disclosure. 2E provides the same advantage offered by 2D, that being the facilitation of inhalation with increasing frequency and exhalation with decreasing frequency. The seven successive notes C, D, E, F, G, A, and B occurring during the 5.9 second period is intentional, the number 7 being used consistently between both audible and visual presentations. Each note is sustained for a period of approximately 0.84 seconds.

FIG. 2F employs the simple method of counting, that is, the recitation of numbers 1 through 7 and 7 through 1. In this example, as in 2E, changes in breathing cycle occur in between the two highest numbers and two lowest numbers. Again this case offers the advantage of facilitating inhalation with increasing number and exhalation with decreasing number.

Referring now to FIG. 3, an essential embodiment of the present invention involves the adjustment of musical tempo and integration of audible cues into musical scores for the purpose of identifying the beginning and end of the 5.9 second interval such that both singers and or listeners are able to employ the music for purposes of synchronizing their breathing to the audible cues and thereby achieving coherence of their respective heart rate variability cycles. The score of Silent Night 31 is used for this example. In this case, the tempo 32 is adjusted to allow markers to be inserted at 5.9 second intervals while in keeping with the basic tempo of the musical piece. In this example, chime 33, 34, 35, 36, 37 is inserted every 5.9 seconds 38. The chime or equivalent musical cue can be integrated into the music at the time the music is being played or can be mixed in post recording. Of course, the degree to which the marker integrates pleasantly with the score has to do with the tempo of the music and the degree to which it conforms with the 5.9 second interval.

FIG. 4 depicts the application of the 5.9 second breathing interval to the repetition of "mantra", mantra 44, 45, typically being a short verse or phrase of spiritual significance that is repeated over and over again. In this example, the 5.9 second interval 46, 47, is delineated by a chime 41, 42, 43 that occurs at the beginning of each 5.9 second interval. The mantra itself may fill this 5.9 second interval as well as span the interval with different verses.

Because both song and mantra are activities in which groups of people often participate, when music or mantra incorporating breathing cues is utilized the heart rate variability cycles of participants are synchronized. This is a nascent field of investigation about which much will be learned via the application of the present invention.

A discussion of visual presentation methods will now ensue. A similar requirement exists for visual indicators as for audio indicators, that is, it is desirable that the visual indicator communicate as much information as is possible about the 5.9 second cycle to the user. This includes changes from inhalation to exhalation and visa versa, whether the phase is an inhalation phase or an exhalation phase, and progression of the 5.9 second interval. Visual indicators may work alone or in combination with audible presentation methods previously described.

Referring to FIG. 5, the most basic method is represented by 51 which is a simple indication of change of breathing phase, that is, the change from inhalation to exhalation or visa versa. During the inhalation phase, indicator 52 is highlighted, during the exhalation phase indicator 53 is highlighted.

FIG. 6 presents a 13 segment indicator 61 that denotes the change of cycle, the present phase of the cycle, that is, inhalation or exhalation, and progression of the cycle. Inhalation is indicated by the transition from 1 to 7, exhalation is indicated by the transition from 7 to 1. It employs the 7 stage convention as did audio examples 2E and 2F. A second convention is applied to this visual display, this being the association of specific colors with specific numeric stages of progression. This association is depicted in the table 64. Each segment of the 13 segment indicator 61 is illuminated for $\frac{1}{13}$th of the fundamental 5.9 second period or 0.45 seconds.

Because numbers 1, 62, and 7, 63, are representative of both the end of the inhalation phase and the beginning of the exhalation phase, they are highlighted for 2 consecutive beats.

Referring to FIG. 7, these conventions and their relevance to breathing and heart rate variability will now be discussed. Preferred audible and visual embodiments of the present invention employ the 7 stage convention with inhalation occurring on increasing number and exhalation occurring on decreasing number. The 7 stage convention conforms to traditional yogic theory of energy planes or centers that exist in the body. When a subject employs the prescribed breathing method, that is synchronization of their breathing cycle with an external timing reference that is tuned to the natural heart rate variability cycle, the heart rate variability cycle will synchronize with the breathing cycle. When a subject practices this technique for a period of time, there is an internal perception that the energy in the body progresses to these different centers in a fashion consistent with the cycle of breath. That is, as inhalation occurs 71, the energy moves from the lowermost center of the body, corresponding to the number 1, 73, to the uppermost center of the body corresponding to the number 7, 74 via display segments 2, 3, 4, 5 and 6. As exhalation occurs 72, the energy moves from the uppermost center of the body corresponding to the number 7, 74, to the lowermost center of the body corresponding to the number 1, 73 via display segments 8, 9, 10, 11, and 12. As this begins to happen, this energy movement and its location in the body becomes an important dimension of the perceived progression of the breathing cycle. A consistent association of color with number is applied to this display according to table 75. Relative to this specific display, there are 12 segments, 5 of which are paired.

Referring to FIGS. 8, 81 and 82 are simply circular representations of a 7 segment indicator. Sectors are sequentially highlighted from 1 to 7 and 7 to 1. 81 demonstrates the inhalation phase of the cycle and 82 demonstrates the exhalation phase of the cycle. That is, as inhalation occurs 81, the energy moves from the lowermost center of the body, corresponding to the number 1, to the uppermost center of the body corresponding to the number 7. Each sector is illuminated for $1/7^{th}$ of the fundamental 5.9 second period or 0.84 seconds. A consistent association of color and number is applied to this display according to table 83.

As in the case of music or mantra being engaged in simultaneously by multiple participants resulting in group synchronization of the heart rate variability cycle, the same applies to any form of the invention in which a group can participate including audible and visual forms. These might include school rooms, board rooms, concert halls, etc. This might also include wide area groups including local, regional, national, and global participation via television, internet, and radio broadcast. Again, as this is a nascent field of investigation much will be learned in this regard via the application of the present invention.

What is claimed:

1. A method of presenting audible and visual cues to a human for synchronizing a breathing cycle with an external timing reference for purposes of synchronizing a heart rate variability cycle with the breathing cycle, thereby achieving coherence of the heart rate variability cycle, comprising:
   a) generating a human perceptible indication to identify inhalation phases and exhalation phases of the breathing cycle, changes between said inhalation and exhalation phases, progression of said inhalation and exhalation phases in time, and progression of said inhalation phases and exhalation phases relative to a period of time having a combination of the inhalation phases and exhalation phases, the combination having a center frequency, wherein the period of time having the center frequency represents a nominal heart rate variability cycle and generating the human perceptible indication of the progression of the inhalation phases and the exhalation phases employs frequency modulation as the basis of the progression; and
   b) instructing the human to align the breathing cycle with the generated human perceptible indication to synchronize the heart rate variability cycle with the breathing cycle to achieve coherence of the heart rate variability cycle.

2. The method of claim 1 wherein generating the human perceptible indication comprises generating an audible indicator including at least one of an audible pulse, tone, chirp, chime, or tick of short duration to signal a change of the breathing cycle from at least one of the inhalation phases to the exhalation phases and the exhalation phases to the inhalation phases.

3. The method of claim 1 wherein generating the human perceptible indication comprises generating an audible indicator including an audible signal including a frequency modulated tone to identify the inhalation phases and the exhalation phases, the change of the phases, progression of phases in time, and progression of the inhalation phases and exhalation phases relative to the period having the center frequency.

4. The method of claim 1 wherein generating the human perceptible indication comprises generating an audible indicator including an audible signal consisting of musical notes C, D, E, F, G, A, and B playing sequentially within the period of time having the center frequency, C to B denoting inhalation during the inhalation phases and B to C denoting exhalation during the exhalation phases.

5. The method of claim 1 wherein generating the human perceptible indication comprises generating an audible indicator by generating an audible signal including audible cues which are incorporated into a mantra repetition.

6. The method of claim 1 wherein generating the human perceptible indication comprises generating an audible indicator by generating at least one of an audible indicator and a visual indicator in group settings to achieve breathing synchronization and consequent group synchronization of the heart rate variability cycle.

7. The method of claim 6 wherein the audible and the visual indicator are comprised from group settings consisting of local, regional, national, and global internet, television, or radio broadcasts, for purposes of synchronizing the breathing cycle and the consequent group synchronization of the heart rate variability cycle.

8. The method of claim 1 wherein generating the human perceptible indication comprises generating a visual indicator including a plurality of visual indicators representing numbers 1 through 7 where 1 equals red, 2 equals orange, 3 equals yellow, 4 equals green, 5 equals cyan, 6 equals indigo, and 7 equals purple.

9. The method of claim 1 wherein generating the human perceptible indication comprises generating a 14 stage visual indication by using a 12 segment vertically oriented elliptical display, wherein a top segment of the 12 segment vertically oriented elliptical display is highlighted for 2 consecutive stages of the 14 stage visual indication to indicate both an end of the inhalation phases and a beginning of the exhalation phases, respectively, and a bottom segment of the 12 segment vertically oriented elliptical display is highlighted for 2 consecutive stages of the 14 stage visual indication to indicate both an end of the exhalation phases and a beginning of the inhalation phases, respectively.

10. The method of claim 1 wherein generating the human perceptible indication of the progression of the inhalation phases and the exhalation phases includes varying the frequency of the human perceptible indication with the inhalation phases and the exhalation phases.

11. The method of claim 10 wherein varying the frequency of the human perceptible indication includes varying the frequency of the human perceptible indicator between a highest frequency and a lowest frequency indicating the moment of change in the breathing cycle.

12. The method of claim 11 wherein the human perceptible indicator is an audible indicator.

13. The method of claim 10 wherein generating the human perceptible indication of changes between said inhalation and exhalation phases includes providing a lowest frequency of the human perceptible indication to indicate changes from the exhalation phases to the inhalation phases and a highest frequency of the human perceptible indication to indicate changes from the inhalation phases to the exhalation phases.

14. The method of claim 13 wherein providing a lowest frequency of the human perceptible indication to indicate changes from the exhalation phases to the inhalation phases and a highest frequency of the human perceptible indication to indicate changes from the inhalation phases to the exhalation phases facilitates the inhalation phase with an increasing frequency of the human perceptible indication and the exhalation phase with a decreasing frequency of the human perceptible indication.

15. The method of claim 14 wherein generating the human perceptible indication of changes between said inhalation and exhalation phases includes providing a highest frequency of the human perceptible indication to indicate a beginning of the inhalation phases, providing a lowest frequency of the human perceptible indication to indicate a beginning of the exhalation phases, and providing a frequency centered approximately between the highest frequency and the lowest frequency of the human perceptible indication to indicate an end of each of the inhalation phases and the exhalation phases.

16. The method of claim 1 wherein generating the human perceptible indication of the progression of the inhalation phases and the exhalation phases by frequency modulation of the human perceptible indication includes coordinating frequency modulation between an audio indicator and a visual indicator such that both the audio indicator and the visual indicator change frequencies in phase with one another.

17. The method of claim 1, wherein the center frequency is approximately 11.76 seconds.

* * * * *